(12) United States Patent  
Yoshinaga et al.

(10) Patent No.: US 7,862,172 B2  
(45) Date of Patent: Jan. 4, 2011

(54) GAZE DIRECTION MEASURING METHOD AND GAZE DIRECTION MEASURING DEVICE

(75) Inventors: Tomoaki Yoshinaga, Yokohama (JP); Shigeki Nagaya, Tokyo (JP); Chiharu Sayama, Funabashi (JP)

(73) Assignee: Hitachi, Ltd., Tokyo (JP)

(*) Notice: Subject to any disclaimer, the term of this patent is extended or adjusted under 35 U.S.C. 154(b) by 199 days.

(21) Appl. No.: 12/197,351

(22) Filed: Aug. 25, 2008

(65) Prior Publication Data

US 2009/0109400 A1   Apr. 30, 2009

(30) Foreign Application Priority Data

Oct. 25, 2007   (JP) .............................. 2007-277670

(51) Int. Cl.  
  *A61B 3/00* (2006.01)
(52) U.S. Cl. ...................... 351/210; 351/209
(58) Field of Classification Search ................ 351/246, 351/209, 210, 205, 200  
See application file for complete search history.

(56) References Cited

U.S. PATENT DOCUMENTS

| 6,113,237 A * | 9/2000 | Ober et al. .................. 351/210 |
| 6,152,564 A * | 11/2000 | Ober et al. .................. 351/210 |
| 2006/0281969 A1 | 12/2006 | Wang et al. |

FOREIGN PATENT DOCUMENTS

| JP | 2006-141862 | 6/2006 |
| JP | 2006-227739 | 8/2006 |
| JP | 2007-006427 | 1/2007 |
| JP | 2007-6427 | 1/2007 |

OTHER PUBLICATIONS

Jing et al "Gaze Direction Estimation Based on Natural Head Movements" Image and Graphics, 2007, ICIG 2007, Fourth International Conference On, IEEE, Piscataway, NJ Aug. 1, 2007, pp. 672-677.

Erik Pogalin, "Gaze Tracking by Using Fractorized Likelihoods Particle Filtering and Stereo Vision" 3D Data Processing, Visualization, and Transmission, Third International AL Symposium ON, IEEE, PI Jun. 1, 2006 pp. 57-64.

Wang et al "Estimating the eye gaze from one eye", Computer Vision and Image Understanding, Academic Press, US, vol. 98, No. 1, Apr. 1, 2005, pp. 83-103.

(Continued)

*Primary Examiner*—Hung X Dang  
(74) *Attorney, Agent, or Firm*—Antonelli, Terry, Stout & Kraus, LLP.

(57) ABSTRACT

A face horizontal direction measuring unit measures the angle of the face horizontal direction for a face image obtained by an imaging unit. By using information on the radius of the head and information on the shoulder position of the person obtained by the aforementioned measurement, a face vertical displacement measuring unit measures a face displacement in the vertical direction not affected by a head posture. According to the obtained displacement, the face angle in the vertical direction is decided. By using the obtained face direction, the angle of the gaze in the horizontal direction and the eyeball radius are measured. Further, a gaze vertical displacement measuring unit is provided for which measuring the pupil center position against the eyeball center position as the gaze displacement in the vertical direction. This displacement amount is used to measure the gaze angle in the vertical direction.

11 Claims, 11 Drawing Sheets

OTHER PUBLICATIONS

Yoshinaga Tomoaki et al "Examination of Gas Estimation Method Based on Head Geometric Model", Eizo Joho Media Gakkai Gijutsu Kokoku-Ite Technical Report, Eizo Joho Media Gakkai, Tokyo, JP, vol. 29, No. 43, Jul. 1, 2005, pp. 5-8.

* cited by examiner

REFERENCE POSITION
$O_{face}$
C
MEASURING POINT
(1) DISPLACEMENT FROM SHOULDER $b \times d$ $O_{face}$, C, C', $O'_{face}$, $\theta_{face}$, b, c, $b \times d$, y

GAZE DIRECTION MEASURING METHOD AND GAZE DIRECTION MEASURING DEVICE

INCORPORATION BY REFERENCE

The present application claims priority from Japanese application JP2007-277670 filed on Oct. 25, 2007, the content of which is hereby incorporated by reference into this application.

BACKGROUND OF THE INVENTION

1. Field of the Invention

The present invention relates to a gaze direction measuring method for measuring a gaze direction, i.e., into which direction (degrees) a person captured in an image looks and a gaze direction measuring device for executing the method and in particular, to a technique which can effectively be applied to a vertical direction measuring method.

2. Description of the Related Art

By measuring a gaze direction of a person in an image, it is possible to estimate his/her object of interest and psychological state. As a method for measuring a gaze direction of a person, there has been a method for separately measuring a face direction and an eye direction and synthesizing them so as to measure a gaze direction as described in JP-A-2007-6427. This Patent Document discloses a method for measuring a face direction and a gaze direction without requiring a calibration in advance but does not disclose any method concerning the vertical direction.

There has also been a method for measuring a horizontal and a vertical direction of a face by projecting a 3-dimensional model of an object to a characteristic position such as an eye and a mouth as described in JP-A-2006-227739.

SUMMARY OF THE INVENTION

However, the method disclosed in JP-A-2006-227739 should build a 3-dimensional model of a face as a measurement object by using characteristic points such as an eye and a mouth in advance. By projecting the 3-dimensional model onto a 2-dimensional image plane, an image of an arbitrary face direction is generated. The image is compared to an image as the measurement object so as to find the projected image having the largest similarity with the object image and estimate the face direction of the measurement object.

Thus, the conventional method has a problem that it is necessary to build a 3-dimensional model for each of persons in advance for measurement in the vertical direction. The 3-dimensional model used for measurement is built according to the 3-dimensional coordinates of the characteristic points such as an eye, a nose, and a mouth and then a face image texture is pasted on the model. since the face feature greatly differs depending on a person, each time the person to be measured is changed, a new model should be built.

Moreover, for building a model, a face directed to the front is required. When the face is directed to the left or right and no characteristic point appears on the image, it is difficult to paste the texture onto the 3-dimensional model. If a measurement is performed by using an incorrect model, accuracy of the face direction measurement and the gaze direction measurement is significantly degraded.

Moreover, there is a problem that the conventional method is greatly affected by an expression change. When the expression is changed, the positional relationship of the characteristic points and the view of the same person are changed. In this case, even if the 3-dimensional model is rotated to perform a comparison process, the similarity is lost and a large error is caused in the measurement result.

It is therefore an object of the present invention to realize a face/gaze direction measurement not requiring a preparatory calibration by estimating a displacement amount indicating the vertical direction change without using information on a face surface view which greatly changes depending on a person. Furthermore, the estimation of the displacement amount indicating the vertical direction change is realized by using a characteristic point which is moved only slightly by an expression change.

Among the inventions disclosed in the present application, a representative one can be outlined as follows.

That is, the representative invention uses a vertical face displacement measuring unit operating as follows. When a face image is inputted, firstly, an angle of the face in the horizontal direction is measured so as to estimate a reference position which does not fluctuate with respect to a head posture change from radius information on a head and information on a person's shoulder position obtained by the measurement and measure a displacement of a point indicating a vertical-direction change with respect to the reference position. Thus, it is possible to know a vertical-direction displacement and decide the angle of the face vertical direction.

The obtained face direction is used to measure an angle of the gaze horizontal direction and a radius of an eyeball. Similarly, by using a gaze vertical displacement measuring unit, it is possible to obtain a vertical-direction displacement and decide the angle of the gaze in the vertical direction.

A face vertical displacement amount measuring unit can decide a point serving as a reference which will not be varied by a vertical movement of the head portion by making a position at a certain position with respect to the person's shoulder position to be a reference position.

The gaze vertical displacement measuring unit estimates the center position of the eyeball according to the radius of the eyeball, the vertical direction of the face, and the position of the inner and the outer corner of the eye and obtain a gaze displacement in the vertical direction from the eyeball position and the center position of the pupil, thereby deciding the angle in the vertical direction.

In the vertical displacement amount measurements, it is possible to reduce the affects of the expression change and accurately perform the measurements by using the displacement from the shoulder position and the positions of the inner and the outer corner of the eye.

Among the inventions disclosed in the present application, the representative one exhibits an advantage which can be outlined as follows.

That is, the advantage obtained by the representative invention is that it is possible to realize a highly accurate gaze direction measuring method which does not require calibration in advance and is hardly affected by a person's expression change.

BRIEF DESCRIPTION OF THE DRAWINGS

These and other features, objects and advantages of the present invention will become more apparent from the following description when taken in conjunction with the accompanying drawings wherein.

DETAILED DESCRIPTION OF THE EMBODIMENTS

Figure 1:
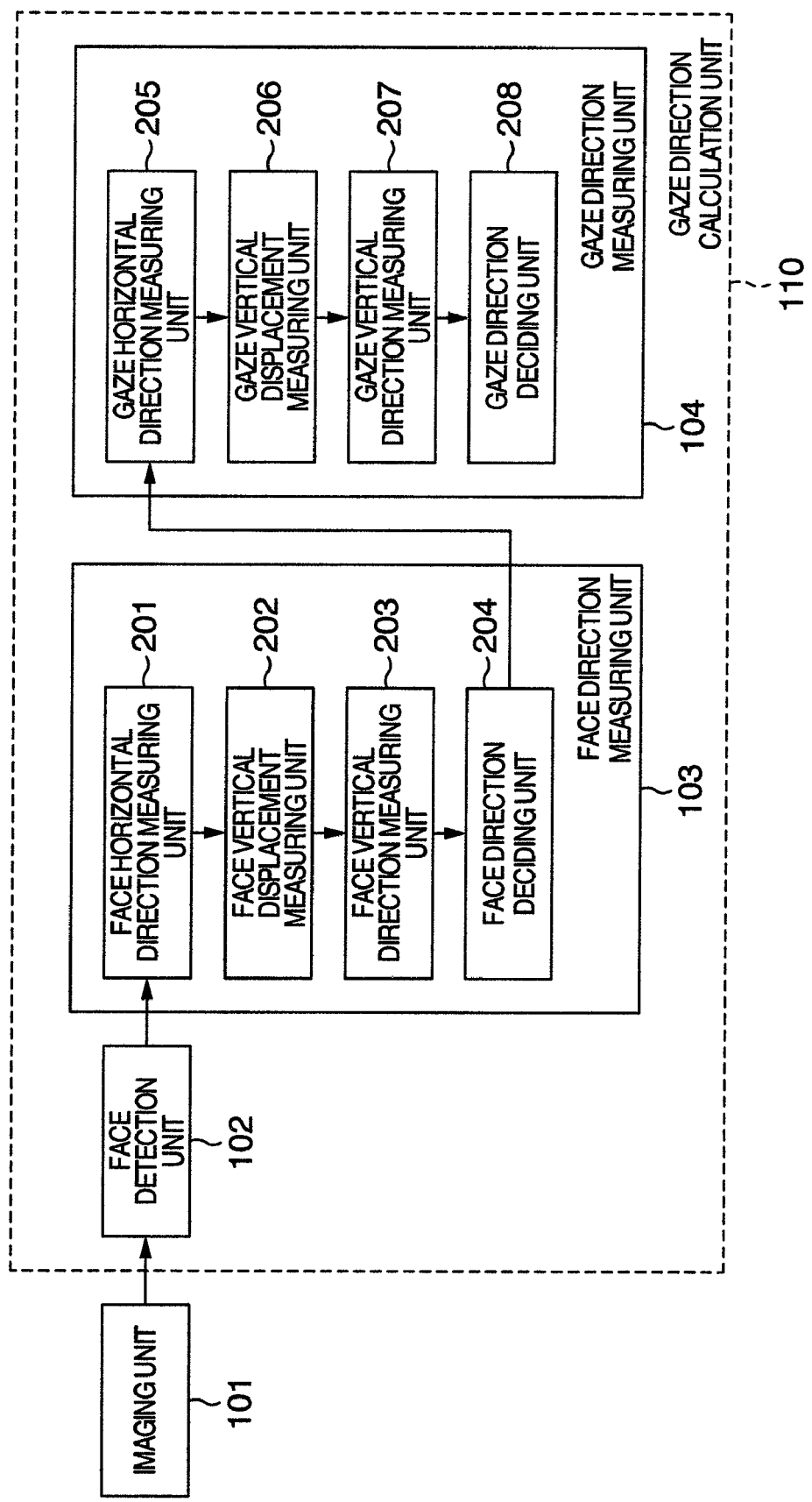
FIG. 1 is a block diagram showing a configuration of a gaze direction measuring device according to a first embodiment of the present invention.

While we have shown and described several embodiments in accordance with our invention, it should be understood that disclosed embodiments are susceptible of changes and modifications without departing from the scope of the invention. Therefore, we do not intend to be bound by the details shown and described herein but intend to cover all such changes and modifications a fall within the ambit of the appended claims.

Description will now be directed to embodiments of the present invention with reference to drawings. It should be noted that in all the drawings, like members are denoted by like reference numerals and their explanations will not be repeated.

Embodiment 1

Referring to FIG. 1, explanation will be given on a configuration of a gaze direction measuring device according to a first embodiment of the present invention.

In FIG. 1, the gaze direction measuring device includes an imaging unit 101, a face detection unit 102, a face direction measuring unit 103, and a gaze direction measuring unit 104. The face detection unit 102, the face direction measuring unit 103, and the gaze direction measuring unit 104 constitute a gaze direction calculation unit 110.

The face direction measuring unit 103 is formed by a face horizontal direction measuring unit 201, a face vertical displacement measuring unit 202, a face vertical direction measuring unit 203, and a face direction deciding unit 204.

The gaze direction measuring unit 104 is formed by a gaze horizontal direction measuring unit 205, a gaze vertical displacement measuring unit 206, a gaze vertical direction measuring unit 207, and a gaze direction deciding unit 208.

The imaging unit 101 is a camera having a function to send captured video data to the face detection unit 102 via a bus, LAN or else.

The face detection unit 102 has a function to perform image processing on the image sent from the imaging unit 101 and detect a face in the image.

The face direction measuring unit 103 acquires an image of the face detected by the face detection unit 102 and measures the face direction. The face direction measurement may be performed by the conventional measuring method. However, if the following measurement method is used, it is possible to perform accurate measurement without performing calibration in advance.

Firstly, the face horizontal direction measuring unit 201 measures the face direction in the horizontal direction. By using the head information obtained by 201, the face vertical displacement measuring unit 202 obtains a face reference position serving as a reference for vertical change of the face. The face vertical direction measuring unit 203 measures the face direction in the vertical direction with the vertical displacement amount with respect to the face reference position obtained by the face vertical displacement measuring unit 202. Lastly, the face direction deciding unit 204 performs correction on the measured angle according to the obtained vertical and horizontal direction change so as to finally decide the face direction.

The gaze direction measuring unit 104 firstly measures the gaze direction in the horizontal direction according to the information on the face direction by the gaze horizontal direction measuring unit 205. Next, according to information on the eyeball obtained by the gaze horizontal direction measuring unit 205, the gaze vertical displacement measuring unit 206 obtains a reference position required for the gaze vertical direction measurement. The gaze vertical direction measuring unit 207 measures the gaze direction in the vertical direction according to the aforementioned information. The gaze direction measurement process is executed for each of the right and left eyes. The gaze direction deciding unit 208 integrates the gaze directions of the right and the left eye so as to decide the final gaze direction.

Thus, for the person image obtained by the imaging unit 101, the face detection unit 102 executes the face detection process. As a result, if a face is detected in the image, the face direction measuring unit 103 measures the face direction.

Lastly, the gaze direction measuring unit 104 measures the gaze direction by using the result of the face direction measurement.

By performing these processes, it is possible to estimate a shape of an eyeball based on the face direction information and measure the gaze direction from the estimated eyeball state. Moreover, since there is a close relationship between the face movement and the gaze movement in the human behavior, it is possible to limit the range of the gaze movement to a certain rage by measuring the face direction, which increases the measurement accuracy.

Figure 2:
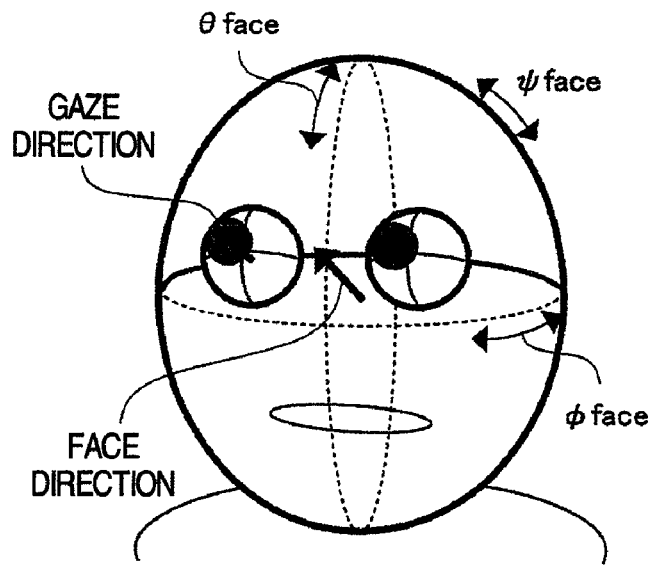
FIG. 2 is a conceptual view of the face direction and the gaze direction measurement by the gaze direction measuring device according to the first embodiment of the present invention.
Figure 3:
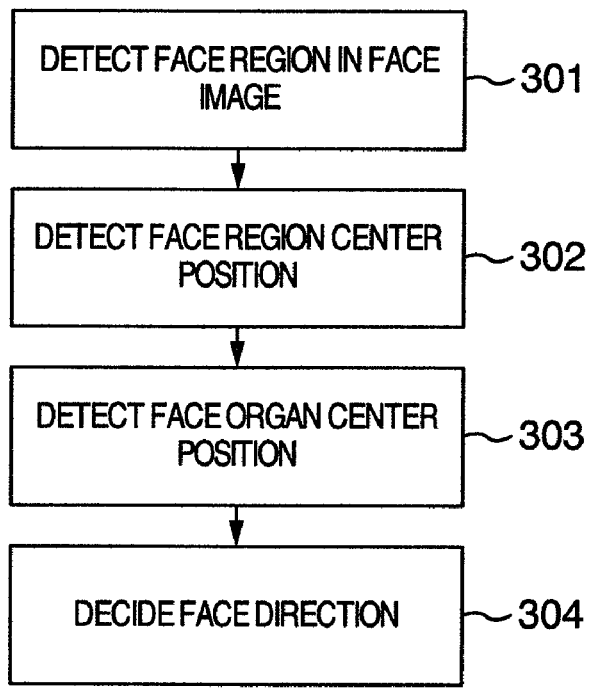
FIG. 3 is a flowchart showing a flow of the face horizontal direction measurement by the gaze direction measuring device according to the first embodiment of the present invention.
Figure 4:
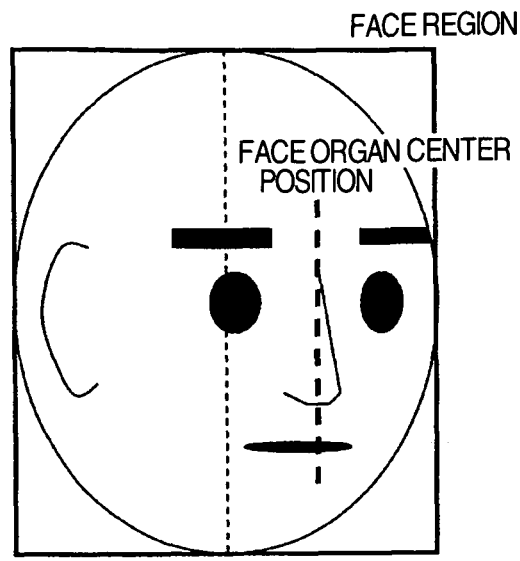
FIG. 4 shows an example of definition of a face region and a face organ center position in a face image in the gaze direction measuring device according to the first embodiment of the present invention.
Figure 5:
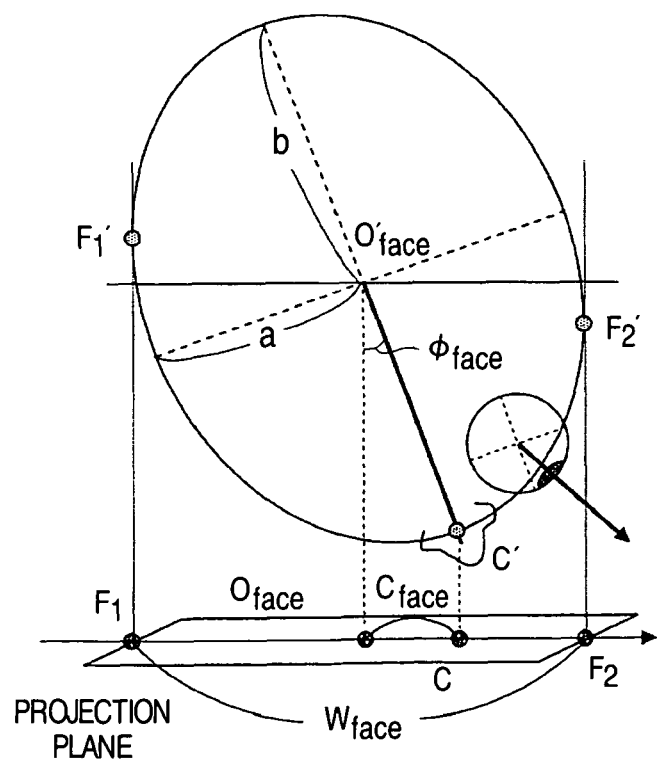
FIG. 5 is a diagram showing an example of a face model for estimating the face horizontal direction by the gaze direction measuring device according to the first embodiment of the present invention.
Figure 6:
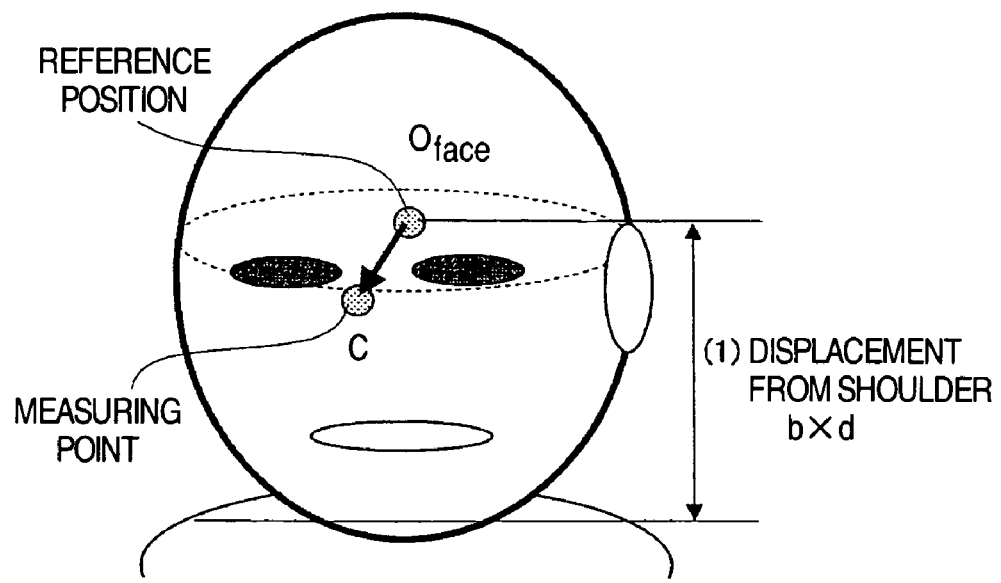
FIG. 6 shows an example of definition of a reference position and a measurement point in a face image by the gaze direction measuring device according to the first embodiment of the present invention.
Figure 7:
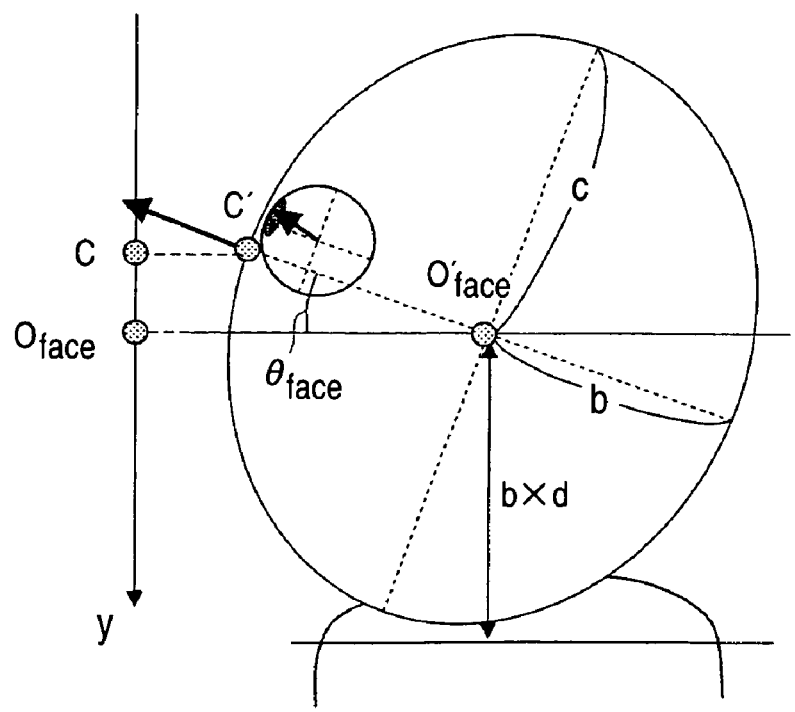
FIG. 7 is a diagram showing an example of a face model for estimating the face vertical direction by the gaze direction measuring device according to the first embodiment of the present invention.
Figure 8:
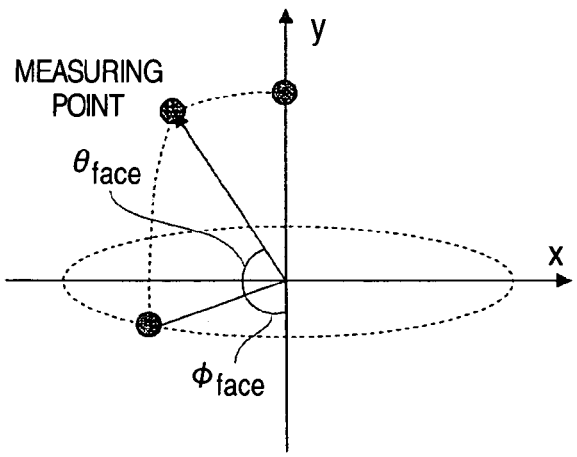
FIG. 8 is a diagram showing a change of the measurement point caused by a vertical/horizontal direction change in the gaze direction measuring device according to the first embodiment of the present invention.
Figure 9:
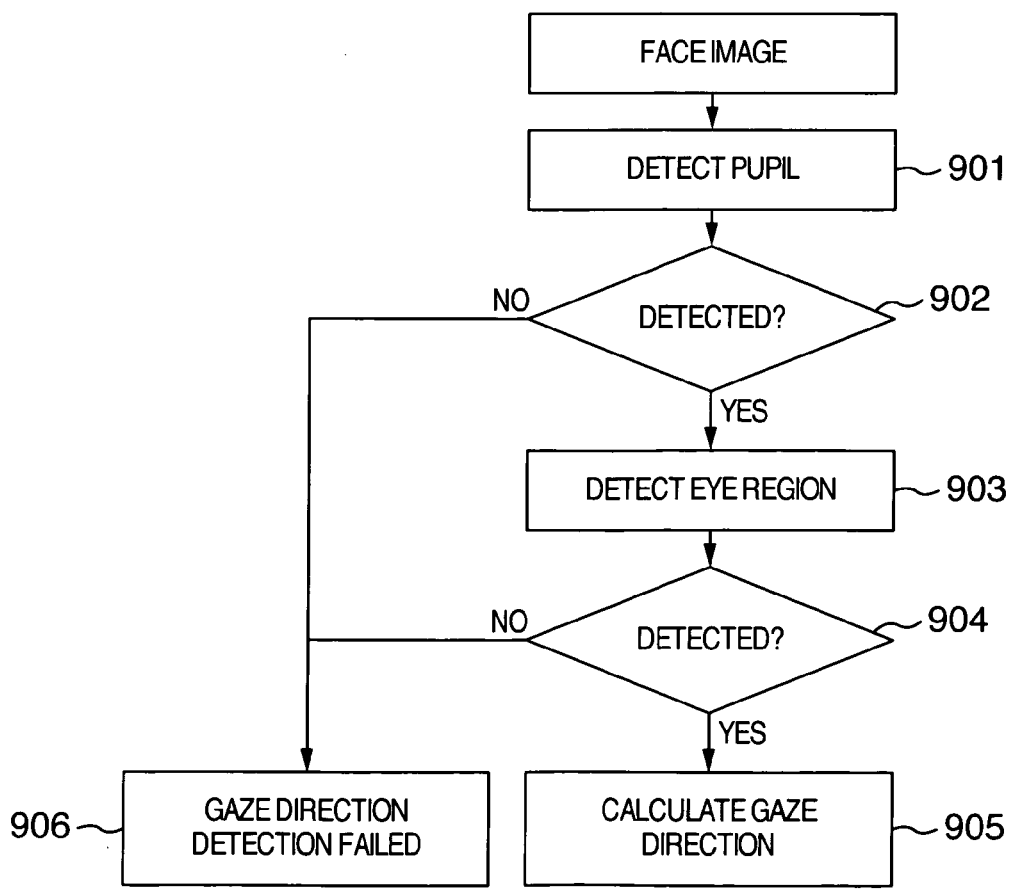
FIG. 9 is a flowchart showing a flow of the gaze horizontal direction measurement by the gaze direction measuring device according to the first embodiment of the present invention.
Figure 10:
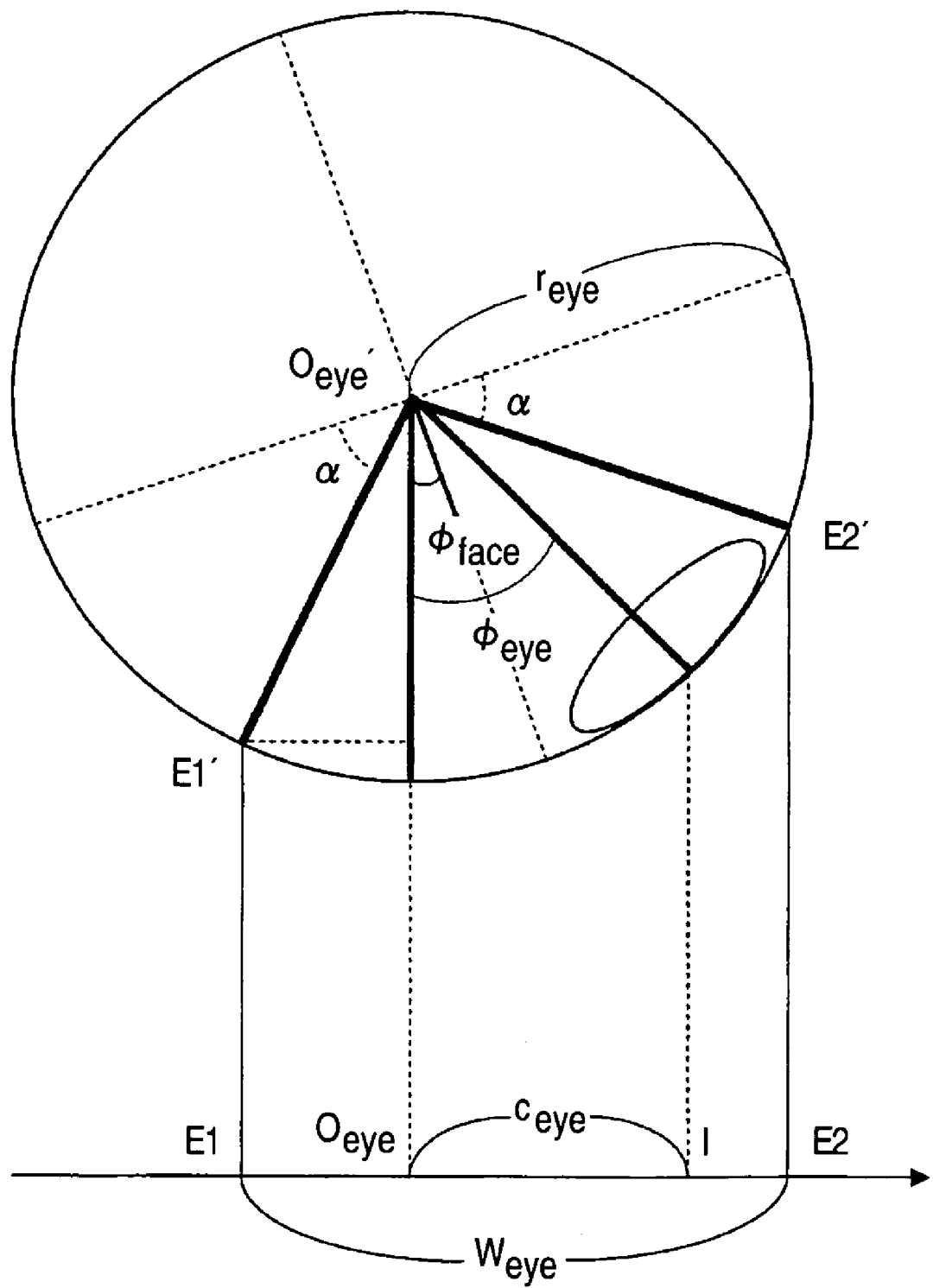
FIG. 10 is a diagram showing an example of an eyeball model for the gaze horizontal direction measurement by the gaze direction measuring device according to the first embodiment of the present invention.
Figure 11:
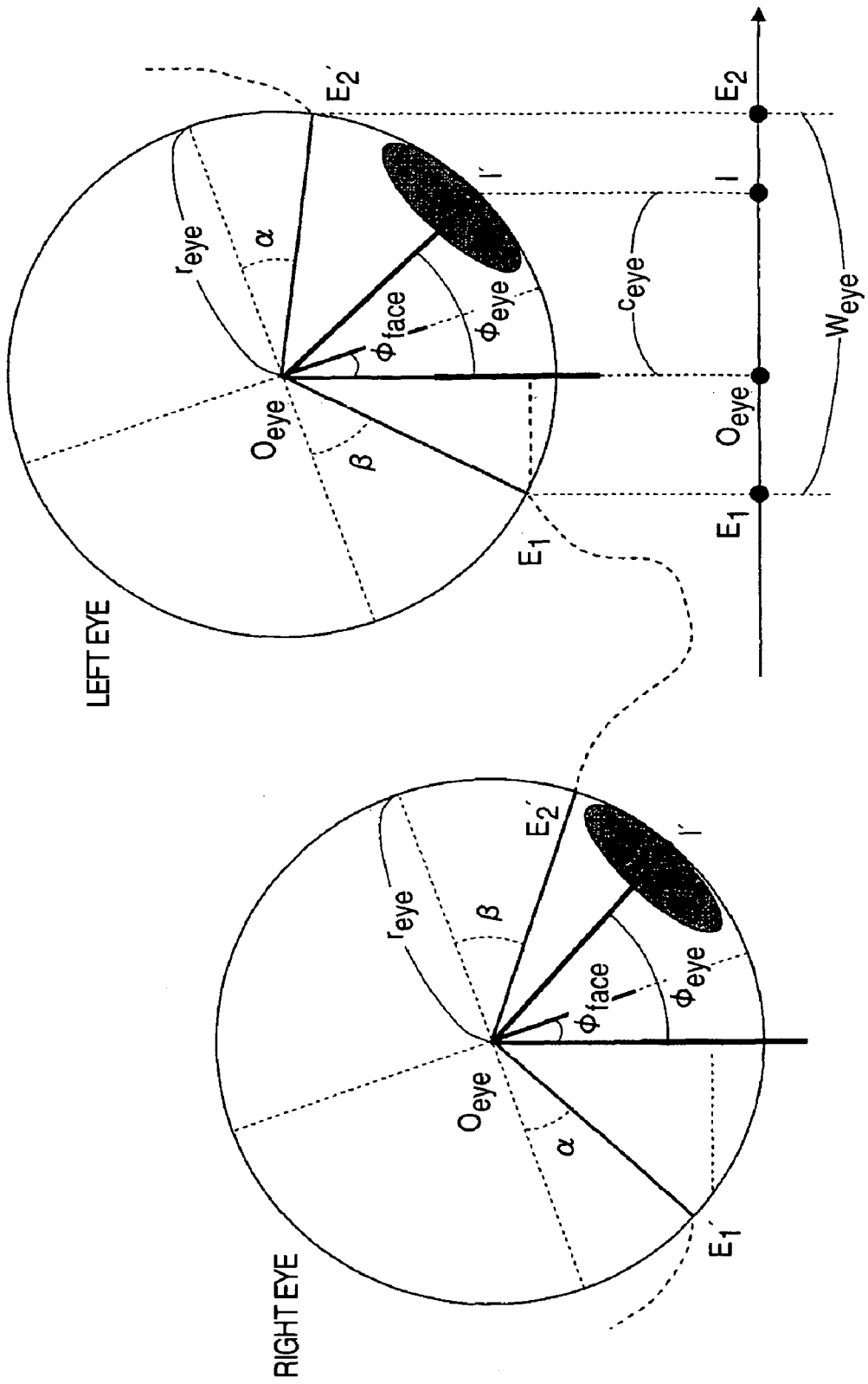
FIG. 11 is a diagram showing an example of an eyeball model for the gaze horizontal direction measurement by the gaze direction measuring device according to the first embodiment of the present invention.
Figure 12:
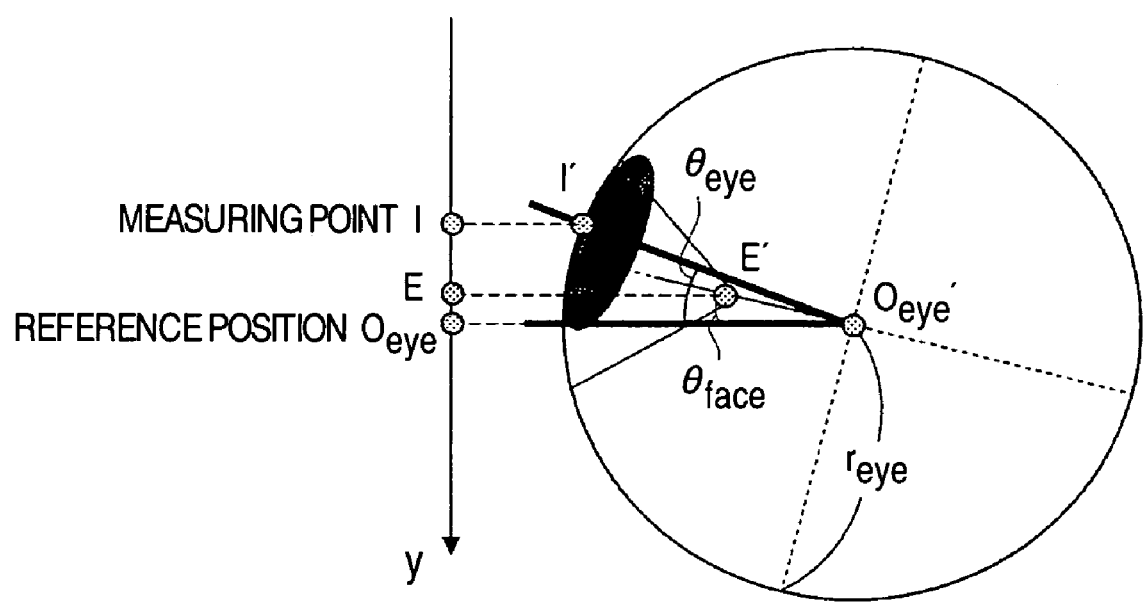
FIG. 12 is a diagram showing an example of an eyeball model for the gaze vertical direction measurement by the gaze direction measuring device according to the first embodiment of the present invention.

Next, referring to FIG. 2 to FIG. 12, detailed explanation will be given on the measuring method in the face direction measuring unit and the gaze direction measuring unit of the gaze direction measuring device. FIG. 2 to FIG. 12 explain the measuring method in the face direction measuring unit and the gaze direction measuring unit of the gaze direction measuring device. FIG. 2 is a conceptual diagram showing a face direction and a gaze direction measurement. FIG. 3 is a flowchart showing a face horizontal direction measurement flow. FIG. 4 shows an example of definition of the center position of the face region and the face organs in a face image. FIG. 5 shows an example of a face model for estimating a face horizontal direction. FIG. 6 shows an example of definition of a reference position and a measuring point in the face image. FIG. 7 shows an example of a face model for estimating the face vertical direction. FIG. 8 shows a change of the measuring point by the vertical/horizontal direction change. FIG. 9 is a flowchart showing a gaze horizontal direction measurement. FIG. 10 shows an example of an eyeball model for a gaze horizontal direction measurement. FIG. 11 is an example of an eyeball model for a gaze horizontal direction measurement. FIG. 12 is an example of an eyeball model for a gaze vertical direction measurement.

In the gaze direction measurement according to the present embodiment, by assuming the model as shown in FIG. 2, it is possible to measure a face horizontal and vertical direction angle, a gaze horizontal and vertical direction angle. It should be noted that the angle in the horizontal direction is denoted by $\phi$, the angle in the vertical direction is denoted by $\theta$, and the face direction is expressed by a subscript "face", and the gaze direction is expressed by subscript "eye". The angles of the face in the horizontal direction and the vertical direction are respectively expressed by $\phi_{face}$ and $\phi_{face}$. Moreover, the face rotation angle $\phi_{face}$ may also be obtained simultaneously.

Firstly, as shown in FIG. 3, the face direction measurement flow in the face horizontal direction measurement unit 1 is performed by the method described in JP-A-2007-6427, for example.

Firstly, in step 301, an accurate face region is estimated from the face image. The face region is estimated by using a method such as extraction of the background difference and the skin color region or Hough transform for ellipse. Here, the face region indicates an rectangular region circumscribing a head portion as shown in FIG. 4.

The center position of the face region is called a face region center position. The face region center position is decided in step 302. Next, in step 303, the face organ center position is detected. The face organ center position is a position of a straight line passing through a center between the eyebrows, a nose bridge, and a convex portion of lips. The face organ center position may be estimated by the positional relationship between the face organs by detecting the face organs such as the eyebrows, the inner corners of eyes, the contour of the nose and the mouth in the face image.

Each of the face organs is detected by using an existing method such as a digitized image of a face image by a luminance value, an edge image, and an image subjected to a separability filter. Step 304 calculates the horizontal direction of the face direction from the obtained face region and the face organ center position.

The face horizontal direction calculation is decided by Expression referencing a face ellipse model shown in FIG. 5. FIG. 5 is an image of a head viewed downward directly above when the face is directed to the rightward in the horizontal direction $\phi_{face}$. Here, the face region appearing in the image has two ends F1 and F2 and the face organ center position is C. The face region center position is the center position $O_{face}$ of the ellipse which is the middle point between F1 and F2. The $w_{face}$ is a width of the face region and $c_{face}$ is the distance between $CO_{face}$. When the semiminor axis of the ellipse model is "a" and the semimajor axis is "b" and the ratio of the "a" and "b" is the face ellipse ratio k, the face direction $\phi_{face}$ can be obtained by Expression 1 given below.

$$\phi_{face} = \sin^{-1} \frac{c_{face}}{(w_{face}/2 - |c_{face}|)k + |c_{face}|} \quad \text{[Expression 1]}$$

In this embodiment, the ellipse ratio k is approximately 1.25. This value is an average head ellipse ratio measured from the statistical data on a person. The value k slightly varies depending on a person but the difference is within a range of 0.1, the affect of which to the face direction accuracy is in an allowed range in this system. Depending on the system configuration, the value k may not be a constant value but it is necessary to actually calculate the face ellipse ratio k.

In this technique, when the imaging unit is arranged at the upper portion and the respective organs cannot be easily detected, by using only the nose which can easily be detected, it is possible to decide the face organ center position. Thus, it is possible to robustly estimate the face direction. Furthermore, it is possible to obtain "b" indicating the depth direction length of the head from the 2-dimensional relationship on the image. Moreover, in this calculation, it is possible to use not only the face organ center position but also the ear position so as to accurately estimate the direction when the face is directed rightward or leftward by more than 45 degrees.

The face vertical displacement measuring unit 202 detects the face reference position as a fixed point with respect to a vertical direction change of the face and a measuring point which varies according to the change of the face direction. The displacement amounts of the two points are made to be displacement amounts caused by the vertical direction change of the face.

As shown in FIG. 6, for example, the face reference position detection means may use a person's shoulder position. Here, the face reference position $O_{face}$ may be defined to be at a position displaced by a certain displacement b×d from the shoulder position. Here, "b" is the depth direction length obtained by the face horizontal direction measuring unit 201 and "d" is a parameter calculating the position of the reference position with respect to the shoulder.

The parameter d is called a reference position calculation constant. It is assumed that a predetermined value is used for the d. The reference position calculation constant d may be an optimal value selected from a plurality of frame information by factorization procedure. Alternatively, it is possible to calculate an optimal value for each examinee by building a system configuration which can perform automatic calibration. As has been described above, by adaptively switching a parameter value for each sequence of the same person, it is possible to further increase the measurement accuracy. By defining the reference position by using a displacement from the shoulder, it is possible to estimate a fixed point not depending on the vertical direction movement of the face and use it for vertical direction measurement.

Furthermore, the reference position thus obtained has an advantage that it is not affected by the face expression change. Moreover, when calibrating the parameter for each of the persons by an automatic calibration process, for example, the calibration may be performed if only the shoulder position and the face direction are known. Accordingly, the calibration may be performed when the face is directed other than the front direction.

Moreover, it is possible to use as the reference position estimating means, for example, a displacement from the position of an ear or the center position of the silhouette of the entire head. Furthermore, the reference position may be decided according to the average of the reference positions obtained from the aforementioned characteristics or the detection result of the characteristics by the image processing. In this case, for example, if the ear could not be detected as the result of the characteristic point detection by the image processing but the shoulder could be preferably detected, it is possible to employ the reference position based on the shoulder position.

The calculation point in FIG. 6 is also decided in the same way. This is decided from the center between the inner corner positions of the both eyes.

According to the ellipse model used for the face vertical direction calculation as shown in FIG. 7, the face vertical direction measuring unit 203 measures the face vertical direction from the reference position $O_{face}$ and the measurement point C. The relationship between the reference position $O_{face}$ and the measurement point C in the image corresponds to the relationship between the $O'_{face}$ and C' on the model. When the displacement of the measurement point C with respect to the $O_{face}$ is $O_{face}C$, the face vertical direction can be measured by Expression 2 given below.

$$\theta_{face} = \sin^{-1} \frac{O_{face}C}{b} \quad \text{[Expression 2]}$$

Here, b represents a radius in the depth direction of the head measured in the horizontal direction. From the reference position with respect to b and the displacement of the measurement position, it is possible to measure the face direction $\theta_{face}$ in the vertical direction.

Since it is possible to estimate the radius by the face horizontal direction measuring unit 201, it is possible to perform the vertical direction measurement by obtaining the reference position not depending on a new face vertical change and a displacement amount of the measurement point reflecting the vertical change. Thus, it is possible to measure a plenty of persons. Moreover, it is possible to perform highly accurate measurement because the reference position is not affected by an expression change.

The face direction deciding unit 204 performs a correction process according to the obtained face direction in the horizontal direction and the vertical direction so as to decide the final face direction. When both of the horizontal direction and the vertical direction have changed, the displacement of the measurement point may be smaller than has been estimated.

FIG. 8 shows measurement points when both of the horizontal direction and the vertical direction have changed.

Here, if the face direction angle is ($\phi_{face}$, $\theta_{face}$), the displacement of the measurement point (x, y)=(b $\sin(\phi_{face})\cos(\theta_{face})$, b $\sin(\theta_{face})\cos(\phi_{face})$).

That is, the absolute value of the displacement amount of x is reduced by $\cos(\theta_{face})$ and that of y is reduced by $\cos(\phi_{face})$. For this, the values divided by each of the values is made to be an actual displacement amount, so as to suppress the affect of the vertical direction change in the horizontal direction measurement and the affect of the horizontal direction change in the vertical direction measurement, thereby performing re-measurement. By the aforementioned correction process, it is possible to obtain a more accurate face direction.

Moreover, by obtaining the face rotation $\psi_{face}$ from the inclination of the line passing through the inner and outer corners of the both eyes or the inclination of the section indicating the center position of face organs, it is possible to perform the correction process by using the face rotation angle.

According to the information on the face direction ($\phi_{face}$, $\theta_{face}$) obtained by the face direction measuring unit 103, the gaze direction measuring unit 104 measures the gaze direction. It should be noted that the gaze direction measuring unit may measure the gaze direction according to the face direction calculated by a measuring method other than the aforementioned measuring method.

As shown in FIG. 9, a flow of the gaze direction measurement by the gaze horizontal direction measuring unit 205 starts in step 901 where the pupil center position is detected in the face image. Step 902 branches the condition according to the number of pupils detected in step 901.

If detection of both of the right and left pupils fails, the gaze direction detection fails and the process is terminated in step 906 because it is impossible to perform measurement. If detection of one or both of the pupils is successful, control is passed to step 903 in the flow.

According to the pupil position obtained in step 902, step 903 obtains an eye region to which each of the pupils belongs. In step 904, the condition of the eye region detected in step 903 is branched. If the eye region cannot be detected correctly, the gaze direction detection fails. If one of the eye regions is detected correctly, control is passed to step 905, where the gaze direction in the horizontal direction is calculated from the pupil center position and the eye region.

Here, explanation will be given on the method for calculating the gaze direction performed in step 905. For this, calculation is performed by using an expression based on the eyeball model shown in FIG. 1 by using the information on the pupil position and the eye region obtained in steps 901 and 903.

The most part of the eyeball is covered with a skin and only a retina portion actually appears as the eye region in the image. In FIG. 10 the retina portion is an arc portion defined by E1' and E2'. Assume that each of the E1' and E2' is at a position of angle $\alpha$ from the horizontal line of the eyeball.

In FIG. 10, $O_{eye}$ and I are the eyeball center position and the pupil center position on the image, respectively, and $O_{eye}'$ is the actual center of the eyeball. $\phi_{face}$ is the angle of the face direction obtained by the face direction detection, $\phi_{eye}$ is the angle of the gaze direction, $W_{eye}$ is the width of the eye region in the image, and $C_{eye}$ is the length of the eyeball center position and the pupil center position on the image. Here, the gaze direction angle $\phi_{eye}$ is decided by Expression 3 given below. Here, the angle $\alpha$ of concealed portion of the eyeball is assumed to be a known value.

$$\sin\phi_{eye} = \frac{2\cos\phi_{face}\cos\alpha}{w_{eye}}(I-E_1) - \cos(\alpha+\phi_{face})$$ [Expression 3]

It should be noted that in Expression 3, $C_{eye}$ is expressed by I–E1. This also applied to Expression 4 and Expression 5 given which will be detailed later.

Moreover, it is also possible to calculate the gaze direction by assuming that the angle of the concealed portion of the eyeball is different between the center side and the outer side of the face. Here, the eyeballs of the both eyes can be shown as in FIG. 11. The angle of the concealed portion at the center side of the face is β and that of the outer side is α. When an expression is established like Expression 2, different expressions are obtained for the right and the left eye. The angle $\phi_{eye}$ of the gaze direction of the left eye can be obtained from Expression 4 given below.

$$\sin\phi_{eye} = \frac{(I-E_1)\cos(\alpha-\phi_{face}) + (1-E_2)\cos(\beta+\phi_{face})}{w_{eye}}$$ [Expression 4]

Similarly, the angle of the gaze direction of the right eye can be obtained from Expression 5 given below.

$$\sin\phi_{eye} = \frac{(I-E_1)\cos(\beta-\phi_{face}) + (I+E_2)\cos(\alpha+\phi_{face})}{w_{eye}}$$ [Expression 5]

As the concealed portions α, β of the eyeball, known values (such as α=33, β=40) are used. This can also be estimated from a value of radius of an ordinary eyeball and a value of the position of the eye region on an image.

Moreover, the gaze horizontal direction measuring unit 205 uses Expression 6 given below to calculate the value of the eyeball radius $r_{eye}$ which is used by the gaze vertical displacement measuring unit 206 and the gaze vertical direction measuring unit 207 which will be detailed later.

$$r_{eye} = \frac{w_{eye}}{\cos(\alpha-\phi_{face}) + \cos(\beta+\phi_{face})}$$ [Expression 6]

Next, the gaze vertical displacement measuring unit 206 detects the reference point and the measurement point required for gaze direction measurement in the vertical direction.

FIG. 12 shows a gaze direction measurement model in the vertical direction, the reference position and the position of the measurement point. The gaze direction measurement model shown in FIG. 12 is one when the eyeball is viewed from the left side of the head. The gaze reference position $O_{eye}$ is at the center position of the eyeball and the measurement point is the center I of the pupil. It should be noted that the measurement point I is assumed to have been detected in the pupil detection by the gaze horizontal direction measuring unit 205.

The gaze reference position is decided from the heights of the inner corner and the outer corner of the eye. The point E' shown in FIG. 12 corresponds to E1' and E2' in the horizontal direction measurement model of FIG. 11 which express the positions of the inner corner and the outer corner of the eye. Assume that the y-coordinates of the inner corner and the outer corner of the left eye are E1 and E2, respectively. Then, it is possible to obtain y-coordinate $O_{eye}$ of the gaze reference position $O'_{eye}$ on the image plane by using Expression 7 given below.

$$O_{eye}=(E_1+r_{eye}\cos\beta\sin\theta_{face}+E_2+r_{eye}\cos\alpha\sin\theta_{face})/2$$ [Expression 7]

Similarly, the gaze reference position of the right eye $O_{eye}$ can be obtained by using Expression 8 given below.

$$O_{eye}=(E_1+r_{eye}\cos\alpha\sin\theta_{face}+E_2+r_{eye}\cos\beta\sin\theta_{face})/2$$ [Expression 8]

Expression 7 and Expression 8 respectively estimate the reference positions from the heights of both corners of the eye E1 and E2 and the face angle in vertical direction and express that the average value is the final reference position. It is also possible to obtain the reference position by using only one of E1 and E2. For example, when the face is turned to the right or left side, one of the corners is concealed. In such a case, only the corner viewed is used to obtain the reference position.

The gaze vertical direction measuring unit 207 decides the gaze direction in the vertical direction from the obtained gaze reference position $O_{eye}$ and the measurement point I. If the displacement of the measurement point I against the gaze reference position $O_{eye}$ is $O_{eye}I$, it is possible to obtain the angle $\theta_{eye}$ of the gaze direction in the vertical direction by Expression 9 given below.

$$\theta_{eye} = \sin^{-1}\frac{O_{eye}I}{r_{eye}}$$ [Expression 9]

By defining the measurement model shown in FIG. 12, it is possible to estimate the gaze reference position (the eyeball center position in the y-coordinate system) by using the eyeball radius obtained by the horizontal direction measurement and the y-coordinate values of the inner and the outer corner of the eye and measure the gaze direction in the vertical direction from the displacement of the pupil center against the reference position. In the present embodiment, it is possible to estimate the eyeball center position without being affected by opened/closed state of the eyelid. Accordingly, it is possible to use the displacement of the eyelid for estimating the pupil displacement, which enables an accurate measurement.

The gaze direction deciding unit 208 decides the final gaze direction from the gaze directions of the both eyes. If the gaze horizontal direction measuring unit 205 cannot detect the pupil/eye region and the gaze direction detection fails, it is impossible to perform the measurement.

If the gaze direction of one of the eyes has been measured successfully, the gaze direction of the eye is employed as the final gaze direction. If the gaze directions of both eyes have been measured successfully, the gaze directions of the both eyes are weighted and added so as to decide the final gaze direction. It is assumed that the weight applied to the gaze direction is decided according to the face direction.

When the face is directed rightward, the right eye hardly appears on the image and the weight on the left eye is increased so that the gaze direction information on the left eye is the main gaze direction. When the face is directed to the front, the gaze direction is decided by the average of the two eyes. It should be noted that the decision of the gaze direction of the both eyes is performed for each of the vertical direction and the horizontal direction.

Thus, it is possible to measure the gaze direction in the horizontal and vertical direction for a person in single-eye camera image without requiring calibration in advance. Furthermore, in the present embodiment, since the face direction measurement does not use the feature of eyes and the mouth which may fluctuate, it is possible to perform robust face direction measurement not affected by an expression change. Moreover, the gaze direction measurement does not use opened/closed state of the eyelid and accordingly, it is possible to accurately measure the gaze direction.

Embodiment 2

Figure 13:
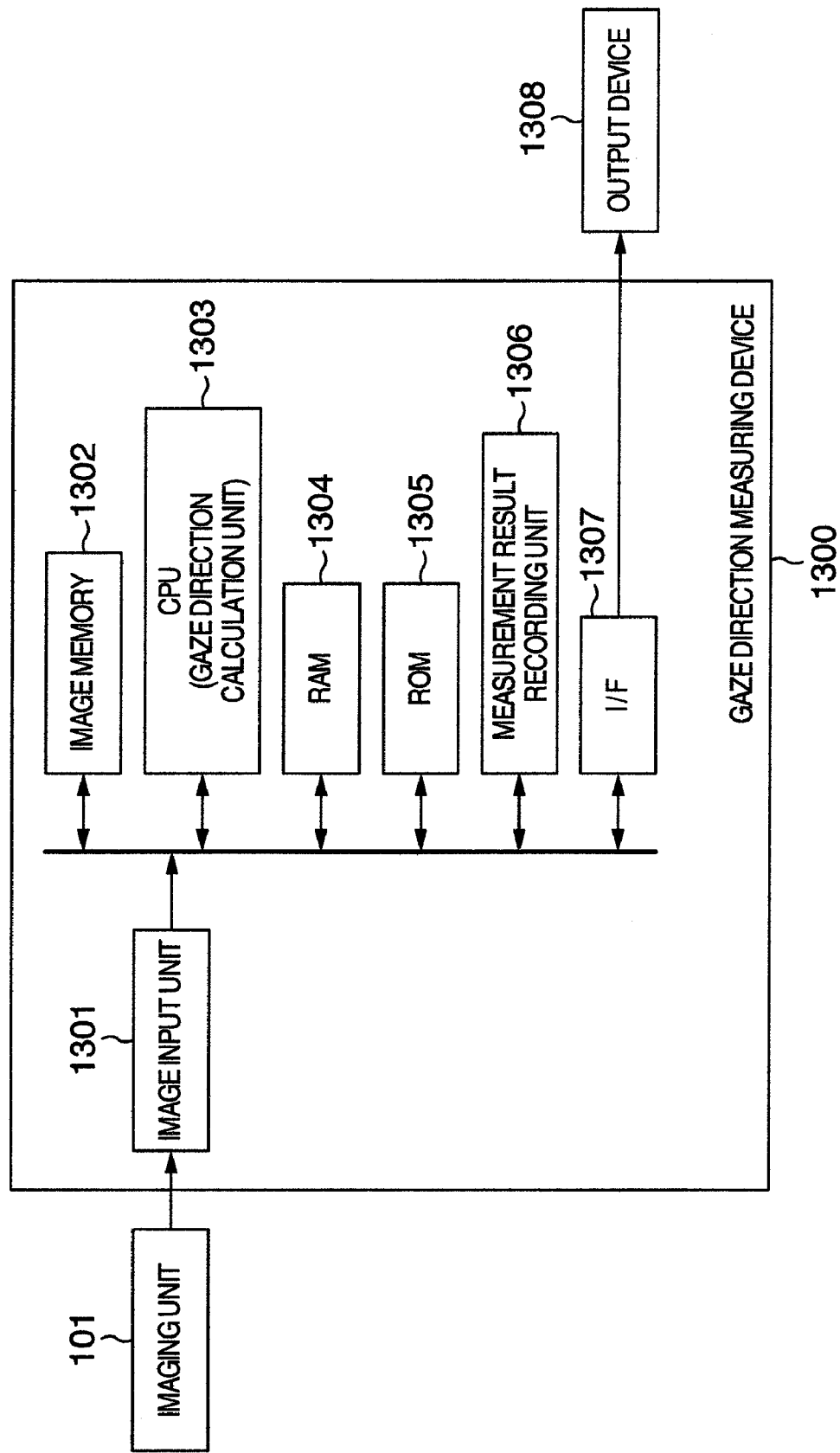
FIG. 13 is a block diagram showing a configuration of a gaze direction measuring device according to a second embodiment of the present invention.

Referring to FIG. 13, explanation will be given on the configuration of a gaze direction measuring device according to a second embodiment of the present invention. FIG. 13 is a block diagram explaining the configuration of the gaze direction measuring device according to the second embodiment of the present invention.

In FIG. 13, the gaze direction measuring device 1300 includes an image input unit 1301, an image memory 1302, a CPU 1303, a RAM 1304, a ROM 1305, a measurement result recording unit 1306, an interface 1307, and an output device 1308.

The gaze direction measuring device 1300 of the present embodiment measures a gaze direction of a person in an image captured by a camera as the imaging unit 101. The CPU 1303 in the gaze direction measuring device 1300 of the present embodiment corresponds to the gaze direction calculation unit 110 of the first embodiment shown in FIG. 1 and executes various calculation processes of the gaze direction calculation unit 110 as programs.

In the present embodiment, the CPU 1303 executes calculation processes to measure the gaze direction according to the measurement method in the gaze direction calculation unit 110.

The gaze direction measurement result for each person and each sequence is recorded in a measurement result recording unit. The measurement result is data-converted into an appropriate form by an interface 1307 and outputted to the output device 1308. Here, the output device may include a display, a printer, and PC.

In this embodiment, the calculation process as the gaze direction measurement device can be performed by an information processing device such as a computer.

Embodiment 3

Figure 14:
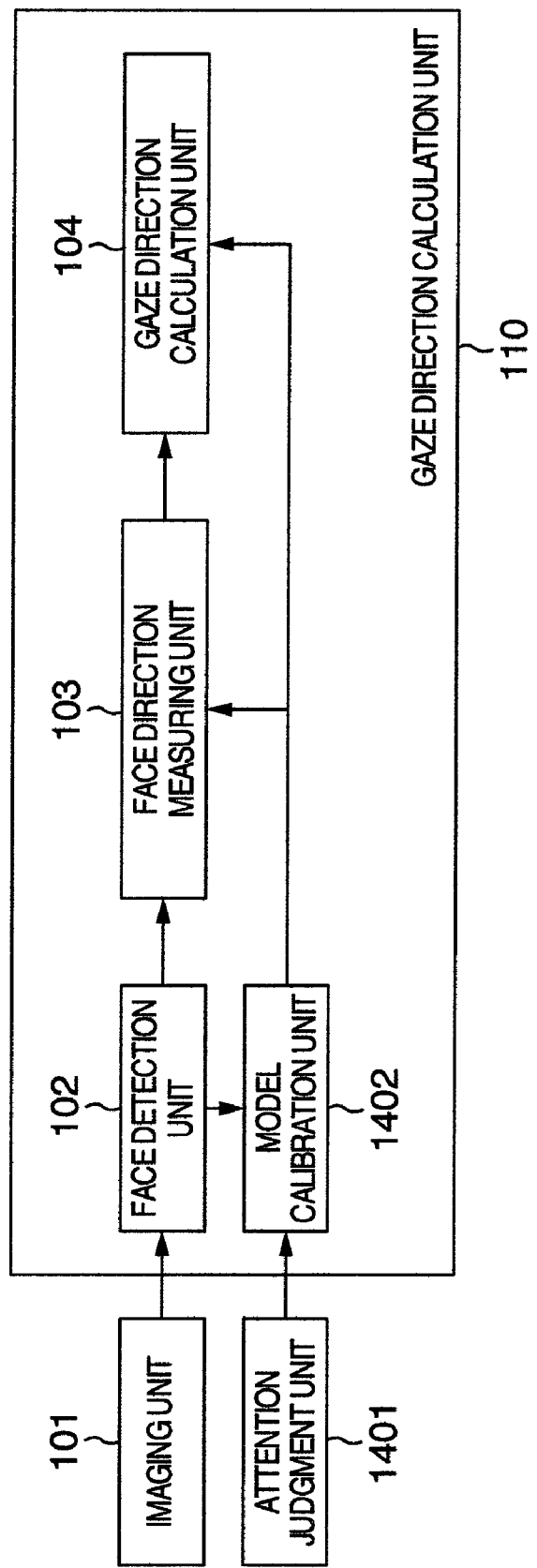
FIG. 14 is a block diagram showing a configuration of a gaze direction measuring device according to a third embodiment of the present invention.

Referring to FIG. 14, explanation will be given on a configuration of a gaze direction measuring device according to a third embodiment of the present invention. FIG. 14 is a block diagram showing the configuration of the gaze direction measuring device according to the third embodiment of the present invention.

As compared to the first embodiment, the third embodiment further includes an attention judgment unit 1401 as an input and a model calibration unit 1402. For example, the model calibration unit 1402 automatically calibrates parameters such as a face reference position calculation constant d in the face vertical direction measurement for each of measurement objects, thereby enabling a more accurate gaze direction measurement.

The attention judgment unit 1401 is formed, for example, by an LED light source projector and an infrared camera. When the gaze is directed to the attention judgment unit 1401, the gaze can be detected. If the positional relationship between the gate judgment unit 1401 and the imaging unit 101 is known in advance, it is possible to know the gaze direction of the face image obtained by the imaging unit when the person gazes at the attention judgment unit 1401. This can be used as calibration data to calibrate the parameter.

The model calibration unit 1402 has a function to calibrate parameters used in the face direction measurement unit 103 and direction measuring unit 104 by using the calibration data obtained by the attention judgment unit 1401.

Next, explanation will be given on the flow in the model calibration unit 1402 by using calibration of the face reference position calculation constant d as an example.

When the attention judgment unit 1401 is gazed, a face image of the frame gazing at the attention judgment unit 1401 is acquired from the face detection unit 102. Calculations are performed in the opposite order as compared to the first embodiment by using the acquired image so as to decide the face reference position parameter d.

Since the gaze direction ($\phi_{eye}$, $\theta_{eye}$) is known, it is possible to obtain the face direction ($\phi_{face}$, $\theta_{face}$) by inverse calculations of Expression 5 and Expression 9 by the gaze direction measuring unit. From the obtained face direction, it is possible to estimate the radius b in the depth direction. By using the b and the face direction, it is possible to obtain a parameter d of the optimal face reference position. The other parameters can also be obtained by inverse calculations in the same way.

If the system requires an online measurement, an average parameter can be used until the parameter calibration by the gaze of the attention judgment unit 1401 is completed. After the parameter is calibrated, the same parameter is used while measurement of the same person is performed.

Moreover, when the system allows an offline measurement such as a client interest analysis, after the parameter calibration by the aforementioned process is complete, it is possible to measure the gaze direction from the first frame having the person. If the attention judgment unit 1401 is viewed at least once within the sequence where the object person appears, the calibration can be performed.

Since this embodiment does not use features which may disappear depending on the angle such as an eye, a nose, and a mouth, it is possible to calibrate the parameter even when the face is directed to other than the front. For this, automatic calibration can be performed even when the imaging unit 101 and the attention judgment unit 1401 are at a slightly separate positions from each other. Thus, the attention judgment unit 1401 can be arranged at the position where an examinee gazes without fail and it is possible to perform automatic calibration while the examinee does not notice this.

Embodiment 4

As compared to the first embodiment, the fourth embodiment further uses a new parameter. The configuration of the gaze direction measuring device of the fourth embodiment is identical to that of the first embodiment.

Figure 15:
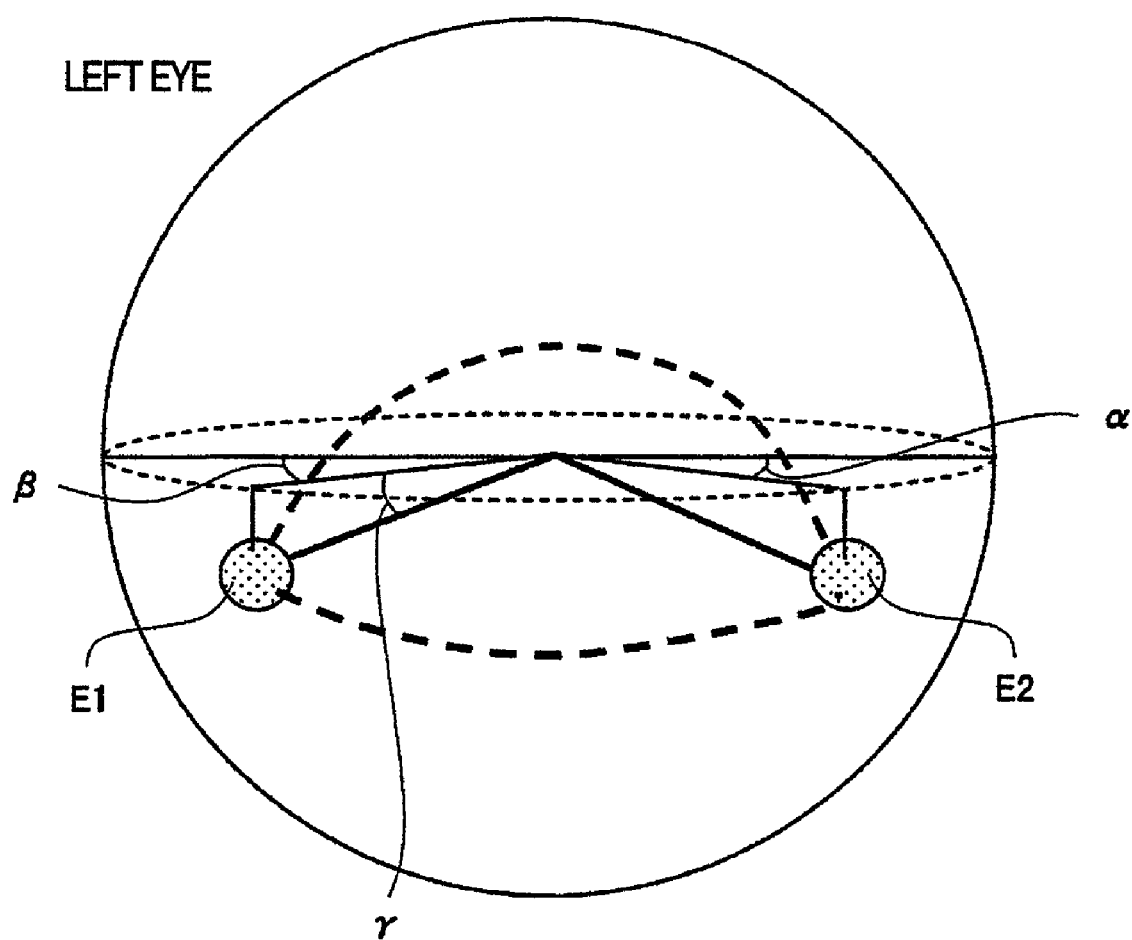
FIG. 15 is a diagram showing an example of an eyeball model for explaining the gaze direction measurement by the gaze direction measuring device according to the fourth embodiment of the present invention.

Referring to FIG. 15, explanation will be given on a gaze direction measurement by the gaze direction measuring device according to the fourth embodiment of the present invention. FIG. 15 shows an example of an eyeball (left eye) model for explaining the gaze direction measurement by the gaze direction measuring device according to the fourth embodiment of the present invention.

In the eyeball model shown in FIG. 15, the inner corner and the outer corner position of an eye are shifted by $\gamma$ degrees in the vertical direction from the center of the eyeball. Thus, by using the new parameter $\gamma$, it is possible to estimate the eyeball shape more accurately and measure the gaze direction with a higher accuracy.

Firstly, the eyeball radius r is calculated from x-coordinates E1x and E2x of the inner corner E1 and the outer corner E2 of the eye and the face direction ($\phi_{face}$, $\theta_{face}$) by using Expression 10 given below.

$$r = \frac{(E_{2x} - E_{1x})}{\cos(\gamma + \theta_{face})\left(\begin{array}{l}\sin(90 - \beta + \phi_{face}) - \\ \sin(\alpha - 90 + \phi_{face})\end{array}\right)} \quad \text{[Expression 10]}$$

From the radius r of the eyeball thus obtained, the position of the center position O of the eyeball is calculated by using Expression 11 given below.

$$O_x = E_{1x} - r\sin(\beta - 90 + \phi_{face})\cos(\gamma + \theta_{face})$$

$$O_y = \{E_{1y} + E_{2y} - r\sin(\gamma + \theta_{face})(\sin(\beta - 90 + \phi_{face}) + \sin(\alpha - 90 + \phi_{face}))\}/2 \quad \text{[Expression 11]}$$

Thus, it is possible to calculate the eyeball radius r and the eyeball center position O so as to estimate a shape of the eyeball. Next, from the center position I of the pupil in the image, the horizontal component $\phi_{eye}$ and the vertical component $\theta_{eye}$ of the gazet direction are calculated by Expression 12 given below.

$$\phi_{eye} = \sin^{-1}\frac{Ix - Ox}{r} \quad \text{[Expression 12]}$$

$$\theta_{eye} = \sin^{-1}\frac{Iy - Oy}{r}$$

Thus, even if the inner corner and the outer corner position of the eye differ depending on the person, it is possible to automatically obtain an optimal parameter γ, thereby measuring the gaze direction more accurately.

The invention made by the present inventor has thus far been explained specifically according to the embodiments. However, the present invention is not to be limited to the embodiments and can be modified in various ways without departing from the spirit of the invention.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A gaze direction measuring method used in a gaze direction measuring device which includes an imaging unit, a face direction measuring unit, and a gaze direction measuring unit and decides a gaze direction of a person captured into an image by the imaging unit, the method comprising steps of:
    measuring, by the face direction measuring unit, an angle of a face direction from a face in the image captured by the imaging unit;
    deciding, by the gaze direction measuring unit, an angle of horizontal gaze direction and a radius of an eyeball according to information on the face direction, a pupil center position in the image, and information on an inner corner and an outer corner of an eye;
    estimating a center position of the eyeball according to the information on the face direction, the information on the inner and the outer corner of the eye, and the information on the eyeball radius;
    measuring a vertical displacement of the pupil according to the center position of the eyeball and the center position of the pupil;
    deciding an angle of the vertical gaze direction according to the information on the vertical displacement of the pupil and the information on the eyeball radius;
    integrating the angles of the gaze directions of both eyes according to the information on the face direction; and
    deciding the gaze direction of the person.

2. The gaze direction measuring method as claimed in claim 1, wherein the gaze direction measurement unit decides a radius of an eye by using as a parameter, information indicating shifts of positions of an inner and an outer corner of the eye from the center of the eye in the vertical direction.

3. The gaze direction measuring method as claimed in claim 1, further comprising:
    a step of measuring, by the face direction measuring unit, a face horizontal direction according to the face in the image captured by the imaging unit;
    a step of estimating a value indicating a vertical displacement of the face according to information on an angle of the face horizontal direction and information on a radius of a head; and
    a step of measuring the angle of the face horizontal direction and according to an angle of the face horizontal displacement.

4. The gaze direction measuring method as claimed in claim 3, wherein the face direction measuring unit detects a position of a shoulder of the person; makes a position displaced by a predetermined distance from the position of the shoulder to be a vertical face reference position; and makes a displacement of the eye with respect to the reference position to be a vertical face displacement.

5. The gaze direction measuring method as claimed in claim 3, wherein the face direction measuring unit makes a position displaced by a predetermined distance from an ear position of the person to be a face reference position; and makes a displacement of the eye position with respect to the reference position to be a vertical face displacement.

6. The gaze direction measuring method as claimed in claim 3, wherein the face direction measuring unit estimates a face reference position from a shape of a silhouette of the head of the person; and makes a displacement of the eye position with respect to the reference position to be a displacement of a vertical face displacement.

7. The gaze direction measuring method as claimed in claim 3, wherein the face direction measuring unit detects silhouette shapes of the shoulder, the ear, the head of the person in the image and switches a feature used for estimating the face reference position according to reliability of the detection process.

8. The gaze direction measuring method as claimed in claim 3, further comprising:
    calculating a measuring error of the radius of the head caused by the change of the angle of the face horizontal direction and the change of the angle of the face vertical direction;
    deciding the face horizontal direction and the face vertical direction according to the corrected radius of the head.

9. A gaze direction measuring device comprising:
    an imaging unit;
    a face horizontal direction measuring unit which measures an angle of a face horizontal direction from a face in an image captured by the imaging unit;
    a face vertical displacement estimating unit which estimates a value indicating a face vertical displacement according to information on an angle of horizontal direction and a radius of a head obtained by the face horizontal direction measuring unit;

a face vertical direction measuring unit which measures an angle of a face vertical direction according to a value of the face vertical direction displacement obtained by the face vertical displacement measuring unit;

a face direction deciding unit which calculates a measuring error of the radius of the head caused by the change of the angle of the face horizontal direction and the change of the angle of the face vertical direction to decide the face horizontal direction and the face vertical direction according to the correct radius of the head;

a gaze horizontal direction measuring unit which decides an angle of a gaze horizontal direction and a radius of an eyeball according to information on the face direction, a pupil center position in the image, and information on an inner corner and an outer corner of an eye;

a gaze vertical displacement measuring unit which measures a value of vertical displacement of the pupil according to the information on a radius of the eyeball obtained by the gaze horizontal direction measuring unit and the face direction;

a gaze vertical direction measuring unit which decides an angle of a gaze vertical direction according to information on the vertical displacement of the pupil; and a gaze direction deciding unit which integrates the angles of the gaze directions of both eyes according to the information on the face direction so as to decide the gaze direction of the person.

10. The gaze direction measuring device as claimed in claim 9, wherein the gaze horizontal direction measuring unit decides a radius of an eyeball by using as a parameter, information indicating a vertical shift of the inner and the outer corner of the eye from the center of the eyeball.

11. The gaze direction measuring device as claimed in claim 9, the device further comprising:

an attention judgment unit which detects a gaze of a person for a predetermined position; and a model calibration unit which calibrates a parameter used for gaze direction measurement by using a face image upon a particular gaze direction detected by the attention judgment unit.

* * * * *